United States Patent [19]

Hirohashi et al.

[11] Patent Number: 4,683,200
[45] Date of Patent: Jul. 28, 1987

[54] MONOCLONAL ANTIBODY TO HUMAN CANCER ANTIGEN AND METHOD FOR PRODUCING SAME

[75] Inventors: Setsuo Hirohashi, 5-6 Goban-cho, Chiyoda-ku, Tokyo; Yukio Shimosato, 4-26-1 Minami-Ogikubo, Suginami-ku, Tokyo; Masahiko Watanabe, 2-7-4 Minami-Tokiwadai, Itabashi-ku, Tokyo, all of Japan

[73] Assignees: Setsuo Hirohashi; Yukio Shimosato; Masahiko Watanabe; Nippon Kayaku Kabushiki Kaisha, all of Tokyo, Japan

[21] Appl. No.: 732,406

[22] Filed: May 9, 1985

[30] Foreign Application Priority Data

May 17, 1984 [JP] Japan ................................. 59-97549
May 22, 1984 [JP] Japan ................................ 59-101769

[51] Int. Cl.$^4$ .................... C12P 21/00; C12N 5/00; C12N 15/00; A61K 39/00
[52] U.S. Cl. ........................................ 435/68; 435/70; 435/172.2; 435/240; 435/241; 435/948; 530/387; 530/388; 424/88; 424/93; 935/89; 935/93; 935/95; 935/104; 935/106; 935/107; 935/108; 935/110
[58] Field of Search ...................... 435/68, 172.2, 240, 435/70, 241, 948; 260/112 R; 935/89, 90, 92, 93, 95, 102–104, 106–108, 110; 530/387, 388; 424/88, 93; 436/548

[56] References Cited

U.S. PATENT DOCUMENTS 4,172,124 10/1979 Koprowski et al. ................... 424/85
4,349,528 9/1982 Koprowski et al. ..................... 424/1
4,584,268 4/1986 Ceriani ..................................... 435/7

OTHER PUBLICATIONS

Shimosato, Y. et al., Journal of the National Cancer Institute, 56(6): 1251–1260 (1976).
Watanabe, M. et al., JPN J Cancer Res. (Gann) 76(1): 43–52 (1985), cited in Bio. Abstract 80060134.
Gangopadhyay, A. et al., Cancer Research, 45(4): 1744–1752 (1985), cited in Bio. Abstract 79106293.
Combs, S. G. et al., J. Histochem. Cytochem. 32(9): 982–988 (1984), cited in Bio. Abstract 79005577.
Wagener, C. et al., Int. J. Cancer, 33(4): 469–476 (1984), cited in Bio. Abstract 78045108.
Pak, K. Y. et al., Molec. Immunol. 20(12): 1369–1378 (1983), cited in Bio. Abstract 77084646.
Arends, J. W., Hybridoma 2(2): 219–230 (1983), cited in Bio. Abstract 77020852.
Wagener C. et al., J. Immunol. 130(5): 2308–2315 (1983), cited in Bio. Abstract 76073688.
Hirohashi, S. et al., Gann 75:485–488 (1984), (Applicants' Publication).

*Primary Examiner*—Margaret Moskowitz
*Attorney, Agent, or Firm*—Cushman, Darby & Cushman

[57] ABSTRACT

Disclosed herein is a monoclonal antibody of the IgM class which reacts with a glycoprotein antigen having a molecular weight by gel filtration of 1,000,000 or higher, the antigenic determinant to be recognized being a sugar chain with a sialic acid residue at the end thereof. The monoclonal antibody has the following characteristics: (1) a reactivity with human cancers of stomach, large intestine, pancreas, breast, lung, biliary duct, uterus and esophagus; (2) a reactivity with normal human submaxillary gland, proximal renal tubule, bronchial gland, squamous epithelial corneum, pancreatic Langerhans' islands, liver cell membrane and duodenal gland; (3) a reactivity with human intestinal metaplastic gastric mucosa; and (4) a non-reactivity with normal human prostate gland, biliary duct and pancreatic duct.

Also provided in the invention is a method for production of monoclonal antibodies. The method comprises administering or implanting cancer cells or tissue to an animal having no thymus, propagating the cells or tissue in the animal, administering T cells or both T cells and B cells to the animal, taking antibody-producing B cells from the animal, fusing the B cells with myeloma cells, selecting fused cells producing an antibody against the cancer cells or tissue, cloning the fused cells, and culturing the cloned fused cell.

3 Claims, No Drawings

MONOCLONAL ANTIBODY TO HUMAN CANCER ANTIGEN AND METHOD FOR PRODUCING SAME

BACKGROUND OF THE INVENTION

This invention relates to a monoclonal antibody, more especially a monoclonal antibody specific for certain cancers. Also, it relates to a new method which can be utlized for effective production of monoclonal antibodies.

Now, production of monoclonal antibodies by cell fusion technique have been established, and many workers have attempted and are still attempting producing new monoclonal antibodies which recognize cancer-related antigens and are useful for diagnosis and/or treatment of cancers.

Among numbers of monoclonal antibodies reported up to now, the monoclonal antibody developed by H. Koprowski et al., CA19-9 (1116NS19-9) is at present expected for practical use in the serum diagnosis of pancreatic cancer. However, this is insufficiently effective for diagnosis of other cancers including gastric cancer.

Generally, the production of monoclonal antibodies recognizing cancer-related antigens has hitherto been performed by administering cancer cells to an animal, for example, mouse or rat, which has the thymus, in other words, which is equipped with both B cells and T cells, to immunize the animal with the cancer cells, fusing antibody-producing cells obtained from the immunized animal with myeloma cells, selecting fused cells producing a desired antibody, cloning the fused cells, and culturing the cloned fused cell. Other method is not availabe nor has been reported.

The present inventors have studied monoclonal antibodies and new methods for production thereof. Now, we have found a monoclonal antibody which highly efficiently reacts with various cancers including gastric cancer, and a novel method for production of monoclonal antibodies which is quite different from conventional methods.

SUMMARY OF THE INVENTION

This invention provides a monoclonal antibody of the IgM class which reacts with a glycoprotein antigen having a molecular weight by gel filtration of 1,000,000 or higher. The antigenic determinant to be recognized by the antibody is a sugar chain having a sialic acid residue at the end thereof.

The monoclonal antibody of the invention has the following properties:

(1) is reacts with human cancers of stomach, large intestine, pancreas, breast, lung, biliary duct, uterus and esophagus;
(2) it reacts with normal human submaxillary gland, proximal renal tubule, bronchial gland, squamous epithelial corneum, pancreatic Langerhans' islands, liver cell membrane and duodenal gland;
(3) it reacts with human intestinal metaplastic gastric mucosa; and
(4) it does not react with normal human prostate gland, biliary duct and pancreatic duct.

Also, there is provided according to the invention a novel method for production of monoclonal antibodies. The method comprises administering or implanting cancer cells or tissue to an animal having no thymus, propagating the cells or tissue in the animal, administering T cells or both T celsl and B cells to the animal, taking antibody-producing B cells from the animal, fusing the B cells with myeloma cells, selecting fused cells producing an antibody against the cancer cells or tissue, cloning the resulting fused cells, and culturing the cloned fused cell.

DESCRIPTION OF THE INVENTION

The term "cells", "tissues" etc. used herein refer to "human cells", "human tissues" etc. unless otherwise noted.

It has been reported that the antigenic determinant recognized by the abovesaid monoclonal antibody, CA19-9, is sialylated-Lewis$^a$. The monoclonal antibody of the invention also recognizes the antigenic determinant which is a sugar chain having a sialic acid residue at the end thereof. However, comparative immunostaining tests of specimens of the same origin with both monoclonal antibodies showed that some specimens readily reacted with the antibody of the invention but not with CA19-9, while other specimens reversely. Further, it has been found that the monoclonal antibody of the invention. reacted with the liver cell membrane, proximal renal tubule of kidney, pancreatic Langerhans' cells and squamous epithelial corneum, while CA19-9 did not, in comparative experiments of the reactivities of both antibodies against normal human tissues. In addition, CA19-9 reacted with the prostate gland, biliary duct and pancreatic duct while the monoclonal antibody of the invention did not. Thus, each antibody recognizes a different determinant.

As shown in examples described hereinafter, the monoclonal antibody of the invention reacts with gastric cancer, colonic cancer, pancreatic cancer, breast cancer, lung cancer, cholangiocarcinoma, uterine cancer and esophageal cancer.

The present monoclonal antibody also reacts with normal tissues of the submaxillary gland, proximal renal tubule, broncial gland, squamous epithelial corneum, pancreatic Langerhans' islands, liver cell membrane and duodenal gland.

Further, the monoclonal antibody reacts with the intestinal metaplastic gastric mucosa.

However, the monoclonal antibody of the invention does not react with normal tissues of the prostate gland, biliary duct and pancreatic duct.

When a tissue specimen of gastric cancer was treated with neuraminidase which is the enzyme that cleaves sialic acid residues, the monoclonal antibody of the invention did not shown the reactivity against such a treated tissue specimen. This indicates that there is a sialic acid residue present in the antigenic site (determinant) to be recognized by the monoclonal antibody.

On the other hand, the monoclonal antibody of the invention did not react against a tissue specimen of gastric cancer which had been treated with periodic acid, indicating that the determinant to be recognized by the present antibody is a sugar chain.

The antigen with which the monoclonal antibody of the invention reacts has a molecular weight of 1,000,000 or higher as determined by gel filtration. In addition, the antigen has an ability to incorporate glucosamine thereinto and, accordingly, it is a glycoprotein.

Thus, the antigen with which the monoclonal antibody of the invention reacts is a glycoprotein having a molecular weight by gel filtration of 1,000,000 or higher and the determinant to be recognized by the monoclonal antibody is a sugar chain having a sialic acis residue at the end thereof.

The monoclonal antibody of the present invention belongs to the immunoglobulin class IgM having a κ chain as L-chain.

The antigen with which the present mnonoclonal antibody reacts is often found in a large amount in sera of patients suffering from gastric cancer, breast cancer, colonic cancer, pancreatic cancer, etc., as well as in the cancer tissues.

Accordingly, the monoclonal antibody of the invention may be useful, in particular, for a highly efficient serum diagnosis of gastric cancer and breast cancer.

The monoclonal antibody of the invention may be produced from a fused cell (hybridoma) formed by cell fusion of a cell producing antibodies, for example, anti-human gastric cancer antibodies, with a myeloma cell.

For example, the monoclonal antibody can be prepared by immunizing an animal, for example, mouse or rat, with an antigen to be recognized by the monoclonal antibody, which may be an isolated antigen or alternatively cancer cells comprising such an antigen or a homogenate thereof, fusing (hydridizing) antibody-producing cells obtained from the immunized animal with myeloma cells, selecting the hydridoma for the production of the monoclonal antibody of the invention, cloning the resulting fused cell (hybridoma), culturing the cloned hybridoma and collecting the antibody produced. Immunization, fusion, selection etc. can be carried out in any conventional manner.

The production of the monoclonal antibody of the invention will be more fully described hereinbelow.

A mouse is immunized with cancer cells such as gastric cancer cells. In addition to mice, murines such as rat or other murine animals may be utilized as an animal to be immunized. Mice are generally preferred. Homogenates of cancer cells or isolated or purified antigens from cancer cells may be utilized for immunization instead of cancer cells per se.

A BALB/c mouse, for example, is immunized by inoculation of cancer cells or homogenate thereof or a purified antigen, several times every few days to few weeks. The amount inoculated may preferably be $10^5$ to $10^8$ cells per mouse for every inoculation.

The spleen is removed from the mouse and antibody-producing cells are collected by centrifugation. These cells have no self-propagating ability. The cells are then hybridized with cells having a self-propagating ability which are preferably selected from myeloma cells. Myeloma cells of the same species that utilized for immunization are most preferable. Preferably, myeloma cells are selected from those producing no antibody. Such myeloma cell lines include, for example, P3-NSI/1-Ag4-1, P3-X63-Ag8, P3-X63-Ag8-U1, P3-X63-Ag8.653, Sp2/0-Ag14, or the like, but they are not limited to these. Other various myeloma cells can also be used in the method.

Hybridization of antibody-producing cells with myeloma cells is carried out by mixing them with a cell fusing agent, such as polyethylene glycol. The ratio of the number of the antibody-producing cells to that of the myeloma cells used is preferably 2:1 to 10:1.

The resulting hybridomas are propagated in tissue culture plates. Antibodies producing in each well are detected on the basis of reactions thereof with various cellular tissues by a conventional method, for example, fluorescent antibody technique or enzyme-labeled antibody technique. Thus, hybridomas producing a desired antibody are selected. Then, hybridomas are cloned using limiting dilution method or other method.

The antibody-producing hybridomas can be cultured in vitro in a culture medium to recover antibodies from the supernatant, or alternatively, they may be cultured in vivo in a living body, for example mouse. In in vivo culture, the hybridomas are intraperitoneally injected to a mouse, a tumor is allowed to grow in the mouse, and antibodies are collected from the ascites or serum of the mouse.

Immunogens which can be used for preparation of the monoclonal antibody of the invention may be cells of gastric cancer or other cancer, but should not specifically be limited.

Antibody-producing cells which can be used for the production of the monoclonal antibody of the invention may be B cells, which are preferably derived from the spleen since B cells circulate in a living body and accumulate in the spleen. However, the method should not necessarily be limited to the spleen and any site wherein B cells are present in a large amount may also be utilized.

Alternatively, the monoclonal antibody of the invention may be prepared by a new method provided according to the present invention, which will be fully described hereinafter.

The antigen with which the monoclonal antibody of the invention reacts is also found in the sera of a patient suffering from a cancer as well as in the cancer tissues. Accordingly, the monoclonal antibody can be useful for the serum diagnosis of a patient suffering from gastric cancer, breast cancer, etc. When the antigen recognized by the monoclonal antibody of the invention abundantly appears in the serum of a patient, the monoclonal antibody can be used for the determination of treating effect or the predication of recurrence.

The monoclonal antibody of the invention can be used for diagnosis of cancer localization by incorporation of a radioactive isotope. Also, a combination of the monoclonal antibody with an anti-cancer agent can be utilized for a missile therapy. The monoclonal antibody of the invention may be helpful for the accurate diagnosis of some lesions which are difficult to differentiate from cancers histologically.

The present invention also provides a novel method for production of monoclonal antibodies which comprises administering or implanting cancer cells or tissue to an animal having no thymus, propagating the cells or tissue in the animal, administering T cells or both T cells and B cells to the animal, taking antibody-producing B cells from the animal, fusing (hybridizing) the B cells with myeloma cells, selecting hybridomas producing the antibody against the cancer cells or tissue, cloning the resulting fused cells (hybridomas), and culturing the hybridoma.

Animals having no thymus include, for example, nude mice nu/nu, nude rats rnu/rnu or others, but any animal except human which has no thymus nor substantial amount of T cells can be utilized in the method of the invention. Usually, a mouse having no thymus may advantageously be employed.

Such an animal having no thymus cannot produce any antibody substantially against a foreign implant in spite of B cells present in its body, since there is produced no substantial amount of T cells in the body. When cancer cells or tissue is administered or implanted to such an animal having no thymus, the cancer cell or tissue may propagate (grow) in the animal.

Cancer cells or tissues which may be used for the method include human or any other animal's cancer cells or tissues. Examples of cancers are gastric cancer, lung cancer, breast cancer, pancreatic cancer, colonic cancer, uterine cancer, esophageal cancer, kidney cancer, rectum cancer, cholangiocarcinoma, thyroid cancer, or the like, but this invention is not limited to these.

The amount of cancer cells or tissues administered or implanted are not specifically limited. Usually, it is preferred to implant one to several pieces of cancer tissues minced into about 1 to 4 square mm in size. More specimens may be implanted. Sites to be implanted may preferably be subcutaneous, intraperitoneal or other. When cancer cells are used, the amount to be administered are preferably $10^5$ to $10^8$ cancer cells.

After administering or implanting cancer cells or tissues, the cancer cells or tissues propagate and a mass of tumor grows as the animal is fed. For example, when cancer tissues of 1 to 4 aquare mm are implanted subcutaneously to a mouse having no thymus, a tumor mass of about 1 cm in the largest diameter is grown in one to a few months.

At the time when the tumor is grown to, for example, about 5 mm to 5 cm in the largest diameter, T cells or both T and B cells are administered to the thymus-deficient mouse having the tumor. The lymphocytes administered are preferably derived from an animal of the same species as the thymus-deficient animal.

The amount of the lymphocytes administered is preferably 0.1 to 5 times the amount of T cells or T and B cells contained in the spleen of one animal of the same species which has the thymus and is accordingly capable of producing antibodies. One administration of the lymphocytes is sufficient for the purpose of this method and there is no necessity of administering them several times.

When administered, the T cells will permit either B cells already present in the animal incapable of producing any antibody or the B cells administered to produce antibodies against the tumor (cancer) in the animal.

After administration of the lymphocytes, the tumor mass will gradually be reduced or disappear. At the time when the mass is reduced to half or smaller in size or disappears, the spleen containing antibody-producing cells is removed from the animal and the spleen cells are hybridized with myeloma cells. These antibody-producing cells are B cells, which circulate in the living body and accumulate in the spleen or other organs. Although B cells are preferably derived from the spleen, the sites wherein B cells are present in a large amount may be utilized.

Hybridization, subsequent selection of hybridomas, culture of hybridomas, and collection of the monoclonal antibodies in the method of the invention may be carried out in the same manner as above-described for the conventional method.

In the novel method of the invention there is not required several or many administrations of cancer cells to animals which is absolutely necessary in the conventional method. Thus, a simpler method is provided according to the invention. The method of the invention utilizes animals in which cancer cells or tissues have already been grown and, therefore, a large amount of cancer cells is present. Accordingly, B cells which produce the antibodies recognizing cancer-related antigens are considered to be produced in a large amount. Further, the selection of desired hybridomas is considered to be carried out with a high efficiency.

DESCRIPTION OF THE PREFERRED EMBODIMENTS

The invention will be more fully illustrated with reference to the following non-limiting examples.

EXAMPLE 1

(1) Production of Monoclonal Antibody:

Human poorly differentiated adenocarcinoma of stomach from a nude mouse to which the carcinoma had been implanted (St-4) was minced into specimens of 2 to 3 mm in size. The specimens were implanted subcutaneously into BALB/c nu/nu mice which are thymus-deficient nude mice having almost no T cell. After about one month and a half the tumor was grown to a mass of 10 mm in maximum diameter.

On the other hand, the spleen removed from a BALB/c nu/+ nude mouse was minced, passed through a stainless mesh and suspended into 0.5 ml of saline. The resulting suspension containing T and B cells was intraperitoneally administered to the BALB/c nu/nu mice carrying the tumor of about 10 mm in size.

The tumor disappeared one month after administration of the lymphocytes. Then, 0.2 ml of homogenates of St-4 was administered intraperitoneally to each BALB/c nu/nu mouse. (This administration may be not necessarily carried out in the method of the invention).

Three days later, the spleen was removed from the mouse.

Cell fusion was accomplished according to the method described by Watanbe et al. in Men-eki Jikken Sosaho (in Japanese) VII, 2963–2967 (1978):

Removed spleen was minced, passed through a stainless mesh, and centrifuged at 1,500 rpm, 200 G. After 50 ml of 0.7% $NH_4Cl$ was added to the obtained precipitate to eliminate red cells, the precipitate was washed twice with RPMI-1640. To $1 \times 10^8$ spleen cells thus obtained, $2 \times 10^7$ (5:1) of mouse myeloma cells, P3-X63-Ag8-U1 (hereinafter referred to as P3U1), which had been washed twice with RPMI-1640, were mixed, and the mixture was centrifuged at 2,000 rpm, 200 G for 10 minutes. After well dividing the precipitated cells, 1 ml of RPMI-1640, 37° C., pH 7:4, containing 45% (W/W) of polyethylene glycol 4,000 (Merck & Co., Inc.) was added and incubated at 37° C. for 8 minutes.

After one minute reaction, RPMI-1640 was gradually added to a final total volume of 40 ml at the end of the hybridization, and the total volume was centrifuged at 1,000 rpm, 100 G. To the precipitated cells there was added 40 ml of RPMI-1640 containing 10% fetal bovine serum, and the resulting cell suspension was cultured at 37° C. in a culture vessel filled with 5% $CO_2$.

After 24 hours, the medium was replaced by HAT medium, which contained hypoxanthine, aminopterin, thymidine and 10% fetal bovine serum, and the culture was distributed into Costar micro culture plate in an amount of 0.2 ml per each well.

On the 10th day, the supernatant was collected and analyzed for the antibody production by staining by enzymelabeled antibody technique of paraffin pieces to which gastric cancer tissues were fixed with formalin.

Hybridomas in the wells positive in production of antibody reactive with cancer were cloned by limiting dilution to 0.6 cells per each well. The initial medium used was HT medium containing hypoxanthine, thymidine and 10% fetal bovine serum to which $5 \times 10^5$ thymus cells per well of BALB/c nu/+ mouse were added as a feeder layer. The initial medium was later replaced by RPMI-1640 medium containing 10% fetal bovine serum.

Cloning by limiting dilution was repeated once again.

For mass culture, hybridomas in one well were increased to 5 wells, 24 wells (Falcon 3008) and finally Falcon tissue culture flask. The obtained supernatant to which 0.1% of $NaN_3$ had been added was stored at 4° C.

(2) Selection of Monoclonal Antibody and Staining of Various Tissues by the Monoclonal Antibody:

Staining of some tissues for the selection of the hybridomas producing the monoclonal antibody and staining of various tissues for the analysis of the monoclonal antibody was accomplished according to the avidin-biotin-peroxidase complex method described by S. M. Hsu et al. in J. Histochem. Cytochem., 29, 577–580 (1981) using paraffin pieces to which the tissues were fixed with formalin:

Specimens of sliced human gastric cancer tissues, other human cancer tissues and normal human tissues fixed by 10% formalin to and embedded in paraffin, which were widely available, were treated with methanol containing 0.3% $H_2O_2$ for 20 minutes after the paraffin was eliminated off. The specimens were then washed with phosphate buffered saline (PBS), and treated with PBS containing 10% normal swine serum for 30 minutes.

The specimens were reacted with a solution containing the antibody, that is, the supernatant which had been obtained in (1) above and diluted tenfold with PBS, about 1 μg/ml, at room temperature for 2 hours, and further reacted at 4° C. overnight. The reaction mixture was washed with PBS for 15 minutes and treated with biotin-bound anti-mouse immunoglobulin, 7.5 μg/ml, for 30 minutes.

The sections were washed with PBS for 15 minutes and then treated with avidin DH-biotin-peroxidase complex at room temperature for 30 minutes. Then, the sections were washed with PBS for 15 minutes and reacted with a diaminobenzidine solution containing 50 mg diaminobenzidine, 0.006% $H_2O_2$, Tris buffer, pH 7.6, for 5 to 10 minues. The cellular nuclei were stained with hematoxylin, mounted in a usual manner and analyzed by a microscopy.

(3) Results:

Reactivities of the produced antibodies in 78 wells among 400 wells were analyzed and one hybridoma was selected which produced the monoclonal antibody reacting with gastric cancer, colonic cancer, pancreatic cancer, breast cancer, lung cancer, cholangiocarcinoma, uterine cancer and esophageal cancer, and the normal submaxillary gland, proximal renal tubule, bronchial gland, squamous epithelial corneum, pancreatic Lagerhans' islands, liver cell membrane and duodenal gland, as well as the intestinal metaplastic gastric mucosa, but not reacting with the normal prostate gland, biliary duct and pancreatic duct.

Reactivities of the monoclonal antibody of the invention which was produced by the hybridoma selected, NCC-St-4 39, with various cancer or normal tissues were analyzed according to the method described in (2) above.

(A) Table 1 shows the results of the reactivity tests of the monoclonal antibody against various cancer tissues.

TABLE 1

| | Reactivities with Cancer Tissues | | | |
|---|---|---|---|---|
| | positive specimen | | positive to total | % of positive |
| cancer tissue | ++[a] | +[b] | specimen | specimen |
| gastric cancer | 33 | 29 | 62/102 | 60.7 |
| colonic cancer | 17 | 9 | 26/26 | 100 |
| pancreatic cancer | 21 | 7 | 28/28 | 100 |
| lung adenocarcinoma | 11 | 5 | 16/17 | 94.1 |
| lung squamous cell carcinoma | 6 | 8 | 14/19 | 73.7 |
| lung large cell carcinoma | 7 | 3 | 10/18 | 55.6 |
| lung small cell carcinoma | 0 | 4 | 4/19 | 21.1 |
| breast cancer | 15 | 7 | 22/27 | 81.5 |

[a] ++: a third or more of the cancer cells being positive
[b] +: less than a third of the cancer cells being positive As shown in Table 1, 100% of colonic cancer and pancreatic cancer, 60.7% of gastric cancer, 81.5% of breast cancer and lung cancer, in particular, 94.1% of adenocarcinoma were reacted with the monoclonal antibody of the invention. The reactions of the monoclonal antobody were often strong with mucus and cell membrane in the positive specimens of adenocarcinoma. In the squamous cell carcinoma, only keratotic area reacted strongly. Further, the reactions were positive with one cholangiocarcinoma specimen among one specimen tested, two uterine cancer specimens among three, one esophageal cancer specimen among one, and one kidney cancer specimen among two.

(B) Table 2 shows the results of the reactivity tests of the mononclonal antibody against various normal tissues.

TABLE 2

| Reactivities with Normal Tissues | |
|---|---|
| Normal Tissue | Positive/Total Specimen |
| submaxillary gland | 5/5 |
| proximal renal tubule | 5/5 |
| bronchial gland | 10/10 |
| squamous epithelial corneum | 10/10 |
| pancreatic Langerhans' islands | 10/10 |
| liver cell membrane | 10/10 |
| duodenal gland | 5/5 |
| prostate gland | 0/5 |
| biliary duct | 0/5 |
| pancreatic duct | 0/10 |
| pancreatic acinus | 0/10 |
| brain | 0/5 |
| nervous tissue | 0/10 |
| smooth muscle | 0/10 |
| striated muscle | 0/10 |
| fatty tissue | 0/10 |
| connective tissue | 0/10 |
| blood vessel | 0/10 |
| lymph node | 0/10 |
| normal gastric mucosa | 0/10 |
| large intestinal mucosa | 0/10 |
| small intestinal mucosa | 0/10 |
| spleen | 0/5 |
| thyroid gland | 0/5 |
| mammary gland | 0/10 |
| testis | 0/3 |
| urinary bladder mucous membrane | 0/5 |
| bone | 0/5 |
| bone marrow | 0/5 |
| cartilage | 0/5 |

Further, the monoclonal antibody of the invention reacted with 11 intestinal metaplastic gastric mucosa specimens among 25 specimens tested.

EXAMPLE 2

The gastric cancer specimen was treated with 0.2 U/ml of neuraminidase at 37° C. for 2 hours prior to the staining by the avidin-biotin-peroxidase complex method in Example 1 (2).

On the other hand, another gastric cancer specimen was treated with 0.5% periodic acid at 37° C. for one hour.

Both treated specimens were tested for reactivities in the same manner as Example 1. No staining was observed.

These results demonstrate that the site (determinant) to be recognized by the monoclonal antibody of the invention is a sugar chain having a sialic acid residue at the end thereof.

EXAMPLE 3

In order to determine the immunoglobulin class of the monoclonal antibody of the invention, the precipitation reactions of the monoclonal antibody with anti-mouse sera of various Ig's were accomplished in agar gel.

Clear precipitation curves were formed in the reactions of the monoclonal antibody with anti-mouse IgM serum and with anti-mouse κ chain serum, but no reaction was occurred in the reactions of the antibody with sera of IgG, IgA, IgD, IgE and λ chain. Thus, the monoclonal antibody of the invention is an immunoglobulin IgM, κ.

EXAMPLE 4

(1) The hybridomas obtained in Example 1 ($1 \times 10^7$ cells) were administered intraperitoneally to BALB/c nu/+ mice which had been treated with pristan. One week later, about 5 ml of ascites were collected and subjected to gel filtration by Sepharose CL-6B. Fractions reacting with IgM were selected in the same manner as Example 3 by Ouchterlony's method.

The purified antibodies were labeled with biotin according to the method described by Guesdon et al. in J. Histochem. Cytochem., 27, 1131-1139 (1979).

(2) After gel filtration of 5 ml serum from a patient suffering from pancreatic cancer in Sepharose CL-6B column, each fraction was distributed in 96 well micro titer plate in an amount of 0.1 ml per well. After 24 hours, each well was blocked with PBS containing 5% bovine serum albumin.

The biotin-labeled antibodies (5 µg/ml) obtained in (1) above were added to the plate and the avidin-biotin-peroxidase complex method was carried out.

The reaction was performed by adding 0.015% $H_2O_2$ to 0.1 M citrate buffer, pH 4.5, containing 1 mg/ml of orthophenylenediamine. Measurements were done by utilizing Dynatech Autoreader, MR580, with O.D. 450.

The antigen recognized by the monoclonl antibody of the invention was detected near the void volume, $V_0$, with their molecular weight being $10^6$ daltons or higher.

EXAMPLE 5

To a culture medium of KATO III, siglet-ring cell carcinoma of stomach, $H^3$-glucosamine was added in a concentration of 15 µCi/ml. After three day culture, the supernatant was recovered and dialyzed to eliminate free $H^3$-glucosamine.

The supernatant was passed in an affinity column coupled with the monoclonal antibody of the invention. The antigen having $H^3$ radioactivity was adsorbed on the column.

These results show that the antigen with which the monoclonal antibody of the invention reacts is a glycoprotein.

EXAMPLE 6

In order to measure the reactions of the monoclonal antibody of the invention with sera of normal men, patients with benign diseases and patients with various cancers, enzyme immunoassay (inhibition EIA) was performed according to the method described in Proc, Natl. Acad. Sci., USA, Vol. 81, pp. 5242-5246, August 1984, "Detection of a pancreatic cancerassociated antigen (DU-PAN-2 antigen) in serum and ascites of patients with adenocarcinoma".

Fifty specimens of normal men were measured and the value of the mean thereof plus a value twice larger than the standard deviation was chosen as a cutoff value.

The results are shown in Table 3.

TABLE 3

| Sera | Reactivities against Various Sera |
|---|---|
| | Positive/Total Specimen |
| normal | 1/50 |
| benign diseases of stomach | 1/37 |
| benign diseases of pancreas | 0/11 |
| benign diseases of liver | 0/31 |
| gastric cancer | 18/28 |
| breast cancer | 14/24 |
| pancreatic cancer | 8/22 |
| colonic cancer | 6/28 |
| lung cancer | 4/17 |
| uterine cancer | 5/16 |

What is claimed is:

1. A method for production of a monoclonal antibody which binds to human cancer cells or human cancer tissue comprising the steps of:
   administering or implanting human cancer cells or human cancer tissue to a murine having no thymus,
   propagating the cells or tissue in the murine having no thymus,
   administering murine T cells or both murine T cells and murine B cells to the murine having no thymus,
   taking antibody-producing B cells from the murine having no thymus,
   fusing said antibody-producing B cells with murine myeloma cells to form hybridoma cells,
   selecting hybridoma cells producing an antibody which binds to the human cancer cells or human cancer tissue,
   cloning the hybridoma cells, culturing the cloned hybridoma cells, and recovering said antibody.

2. The method of claim 1, wherein the murine having no thymus is a mouse and the myeloma cells are derived from a mouse.

3. The method of claim 1, wherein the murine having no thymus is a nude mouse and the myeloma cells are P3-X63-Ag8-U1.

* * * * *